United States Patent
Liu

(10) Patent No.: US 11,065,263 B2
(45) Date of Patent: Jul. 20, 2021

(54) STEROL COMPOSITION IN PUMPKIN SEED OIL AND APPLICATION THEREOF, AND DRUG FOR TREATING BENIGN PROSTATIC HYPERPLASIA

(71) Applicant: Hunan Zhongkewentai Bio-tech co. Ltd, Hunan (CN)

(72) Inventor: Dongbo Liu, Hunan (CN)

(73) Assignee: Hunan Zhongkewentai Bio-tech co. Ltd, Hunan (CN)

( * ) Notice: Subject to any disclaimer, the term of this patent is extended or adjusted under 35 U.S.C. 154(b) by 11 days.

(21) Appl. No.: 16/692,388

(22) Filed: Nov. 22, 2019

(65) Prior Publication Data

US 2020/0085844 A1 Mar. 19, 2020

(51) Int. Cl.
*A61K 36/00* (2006.01)
*A61K 31/575* (2006.01)
*A61P 13/08* (2006.01)
*A61K 36/42* (2006.01)

(52) U.S. Cl.
CPC ............ *A61K 31/575* (2013.01); *A61K 36/42* (2013.01); *A61P 13/08* (2018.01)

(58) Field of Classification Search
CPC ...................................................... A61K 36/00
USPC .......................................................... 424/725
See application file for complete search history.

(56) References Cited

U.S. PATENT DOCUMENTS

2012/0172590 A1* 7/2012 Kallimopoulos ....... A61P 25/00
540/581

* cited by examiner

*Primary Examiner* — Michael V Meller

(57) ABSTRACT

A sterol composition in pumpkin seed oil and an application thereof, and a drug for treating benign prostatic hyperplasia are provided, which relate to a technical field of medicine. The sterol composition in the pumpkin seed oil includes components by weight percentage of: 0.2-2 wt % cholesterol, 0.5-5 wt % campesterol, 1.5-5 wt % β-sitosterol, 15-40 wt % stigmasterol, 20-40 wt % ergosta-7,22-dien-3β-ol, 5-10 wt % lanosterol, and 15-30 wt % cholest-7-en-3β,5α-diol. The sterol composition in the pumpkin seed oil is a pumpkin phytosterol composition extracted from the pumpkin seed oil. Through combining the phytosterol components and controlling a proportion among the components, effects of alleviating and treating prostate diseases are achieved, especially for the benign prostatic hyperplasia.

1 Claim, 5 Drawing Sheets

STEROL COMPOSITION IN PUMPKIN SEED OIL AND APPLICATION THEREOF, AND DRUG FOR TREATING BENIGN PROSTATIC HYPERPLASIA

CROSS REFERENCE OF RELATED APPLICATION

The application claims priority under 35 U.S.C. 119(a-d) to CN 201811553857.0, filed Dec. 19, 2018.

BACKGROUND OF THE PRESENT INVENTION

Field of Invention

The present invention relates to a technical field of medicine, and more particularly to a sterol composition in pumpkin seed oil and an application thereof, and a drug for treating benign prostatic hyperplasia.

Description of Related Arts

BPH (benign prostatic hyperplasia) is a common and frequently-occurring disease in middle-aged and older men. Currently, the benign prostatic hyperplasia is treated mainly through western drug therapy and non-drug therapy. The common western drugs comprise 5α-reductase inhibitors such as finasteride, and a1-adrenergic receptor blockers such as phenoxybenzamine and terazosin hydrochloride tablets. Although having certain therapeutic effects, the western drug therapy has a slow effect and generally requires drug administration for more than six months. Moreover, the western drug therapy has a great side effect on patients, such as postural hypotension, weakness, blurred vision and ejaculation disorder.

For the mild and moderate benign prostatic hyperplasia patients, the conservative western drug therapy has certain therapeutic effects. However, for the severe benign prostatic hyperplasia patients, especially for the patients having much residual urine, the obstruction can be relieved only through operative therapy. The operative therapy will damage the body, and meanwhile the related complications will bring obvious pains to the BPH patients. Therefore, both of the above western drug therapy and operative therapy have limitations.

Currently, the common botanical drugs for treating the benign prostatic hyperplasia comprise: bee pollen extract, namely Prostate; saw palmetto extract, namely Permixon and Prostadyn Sabale capsules available in the market; and African pygeum extract, namely Tadenan. However, all of the above botanical drugs have problems of complex composition, unclear mechanism and slow effect, which cannot well meet the requirements of the patients.

Thus, it is urgent to develop a composition which is able to rapidly, safely and effectively treat the benign prostatic hyperplasia.

SUMMARY OF THE PRESENT INVENTION

In order to solve above technical problems, objects of the present invention are to provide a sterol composition in pumpkin seed oil and an application thereof, and a drug for treating benign prostatic hyperplasia, which is able to rapidly and safely treat the benign prostatic hyperplasia without any side effect.

In order to accomplish the above objects, the present invention adopts technical solutions as follows.

A sterol composition in pumpkin seed oil is provided, comprising components by weight percentage of: 0.2-2 wt % cholesterol, 0.5-5 wt % campesterol, 1.5-5 wt % β-sitosterol, 15-40 wt % stigmasterol, 20-40 wt % ergosta-7,22-dien-3β-ol, 5-10 wt % lanosterol, and 15-30 wt % cholest-7-en-3β,5α-diol.

Preferably, the weight percentages of cholesterol, campesterol, β-sitosterol, stigmasterol, ergosta-7,22-dien-3β-ol, lanosterol, and cholest-7-en-3β,5α-diol are respectively 0.5-1 wt %, 1-3 wt %, 2-3 wt %, 20-35 wt %, 25-35 wt %, 6-8 wt %, and 20-25 wt %.

Preferably, the weight percentages of cholesterol, campesterol, β-sitosterol, stigmasterol, ergosta-7,22-dien-3β-ol, lanosterol, and cholest-7-en-3β,5α-diol are respectively 0.99 wt %, 1.35 wt %, 2.42 wt %, 30.06 wt %, 32.01 wt %, 6.09 wt %, and 24.12 wt %.

Preferably, the sterol composition in the pumpkin seed oil is prepared through steps of: processing the pumpkin seed oil successively with saponification and organic solvent extraction; taking an extraction upper phase as an extraction liquid; washing the extraction liquid, drying and crystallizing; and obtaining the sterol composition in the pumpkin seed oil.

Preferably, a weight content of phytosterols in the sterol composition in the pumpkin seed oil is above 90%.

Preferably, the step of "washing the extraction liquid" particularly comprises steps of: washing the extraction liquid successively with water, ethanol-water solution, water, potassium hydroxide solution and water; removing a lower aqueous phase and keeping an upper organic phase of the extraction liquid.

Preferably, the step of washing the extraction liquid with potassium hydroxide solution and water is repeated for at least one time, until the lower aqueous phase becomes neutral.

The present invention further provides an application of the above sterol composition in the pumpkin seed oil in a drug for treating benign prostatic hyperplasia.

The present invention further provides a drug for treating benign prostatic hyperplasia, comprising a pharmaceutically acceptable adjuvant and an effective dose of the above sterol composition in the pumpkin seed oil.

Preferably, the drug for treating the benign prostatic hyperplasia is in form of solutions, pills, tablets, capsules, powders, pastes or aerosols.

Compared with the prior art, the present invention has beneficial effects as follows.

The sterol composition in the pumpkin seed oil provided by the present invention is a pumpkin phytosterol composition extracted from the pumpkin seed oil, wherein: cholesterol, campesterol, β-sitosterol, stigmasterol, ergosta-7,22-dien-3β-ol, lanosterol, and cholest-7-en-3β,5α-diol are all phytosterols; through combining the phytosterol components and controlling a proportion among the components, the effects of alleviating and treating the prostate diseases are achieved, especially for the benign prostatic hyperplasia.

Through cooperation among the phytosterols in the sterol composition in the pumpkin seed oil, the anti-inflammatory effect and the immunomodulatory effect are achieved. Moreover, the phytosterols in the sterol composition in the pumpkin seed oil show high affinity to the prostate tissues and hormonal activity in the animals or human bodies, so that the genetic expressions of the growth factors related to the benign prostatic hyperplasia are regulated without any hormonal side effect. Furthermore, the sterol composition in the pumpkin seed oil is mainly Δ-7 phytosterol, which is the major substance for inhibiting the benign prostatic hyperplasia. The Δ-7 phytosterol has the effect of inhibiting the 5α-reductase, so as to inhibit the testosterone from transforming into the dihydrotestosterone and inhibit the benign prostatic hyperplasia. The sterol composition in the pumpkin seed oil can inhibit not only the expression of 5α-reductase, but also the genetic expressions of androgen receptor, bFGF (basic fibroblast growth factor) and TGF-β1 (transforming growth factor-β1), which is able to obviously decrease the prostate weight and the prostate index, so that the benign prostatic hyperplasia is recovered.

BRIEF DESCRIPTION OF THE DRAWINGS

In order to illustrate technical solutions of the present invention more clearly, the accompanying drawings for the preferred embodiments or the prior art are simply described as below. Apparently, the accompanying drawings in the following description are only some embodiments of the present invention, and persons of ordinary skill in the art can derive other drawings from the accompanying drawings without creative efforts.

Figure 1:
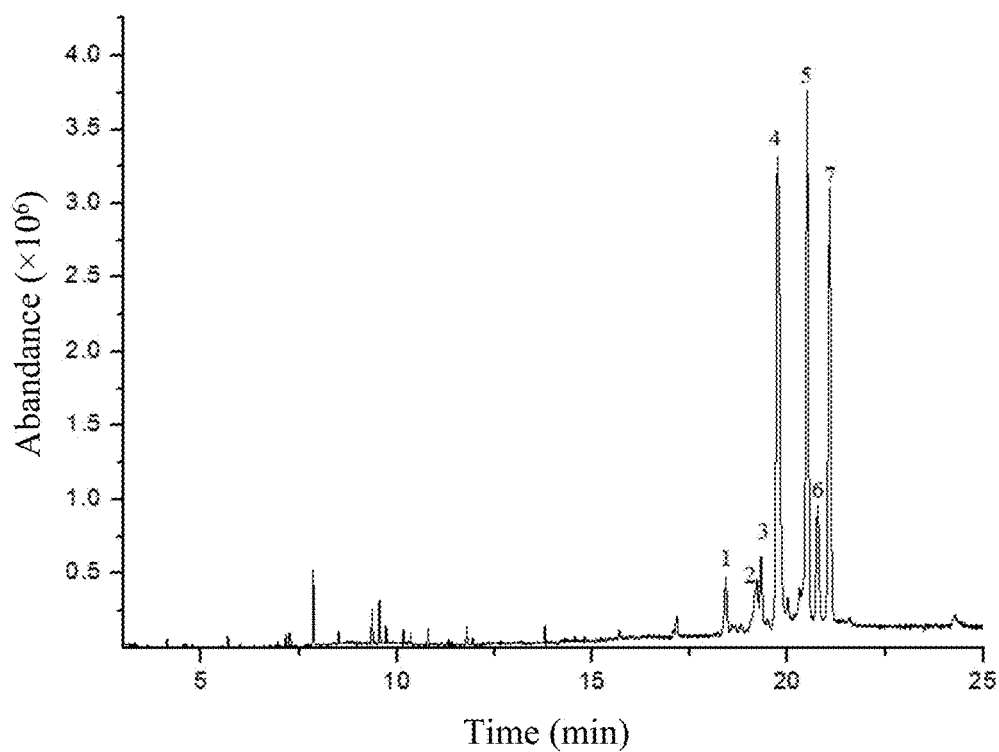
FIG. 1 is a GC-MS (Gas Chromatography-Mass Spectrometer) spectrum of a sterol composition in pumpkin seed oil according to example 1 of the present invention.

In figures: 1: cholesterol; 2: campesterol; 3: β-sitosterol; 4: stigmasterol; 5: ergosta-7,22-dien-3β-ol; 6: lanosterol; and 7: cholest-7-en-3β,5α-diol.

DETAILED DESCRIPTION OF THE PREFERRED EMBODIMENT

In order to illustrate technical problems, technical solutions and beneficial effects of the present invention more clearly, the present invention is further illustrated in detail with accompanying drawings and preferred embodiments as follows. It should be understood that the described preferred embodiments herein are merely for explaining the present invention, not for limiting the present invention.

According to the preferred embodiment, the present invention provides a sterol composition in pumpkin seed oil, comprising components by weight percentage of: 0.2-2 wt % cholesterol, 0.5-5 wt % campesterol, 1.5-5 wt % β-sitosterol, 15-40 wt % stigmasterol, 20-40 wt % ergosta-7,22-dien-33-ol, 5-10 wt % lanosterol, and 15-30 wt % cholest-7-en-3β,5α-diol.

For the cholesterol, a molecular formula is $C_{27}H_{46}O$, a relative molecular mass is 386.35, and a chemical structural formula is:

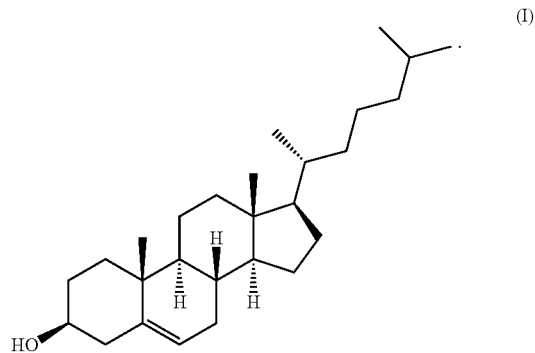

For the campesterol, a molecular formula is $C_{28}H_{48}O$, a relative molecular mass is 400.69, and a chemical structural formula is:

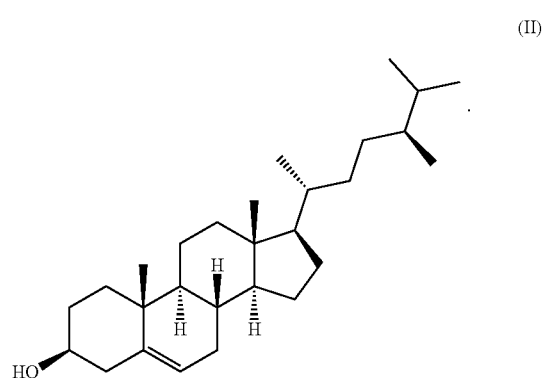

For the β-sitosterol, a molecular formula is $C_{29}H_{50}O$, a relative molecular mass is 414.72, and a chemical structural formula is:

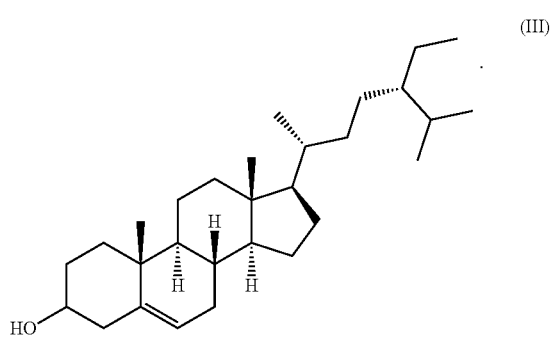

For the stigmasterol, a molecular formula is $C_{29}H_{52}O$, a relative molecular mass is 416.73, and a chemical structural formula is:

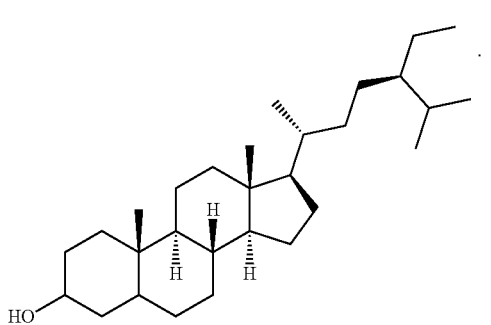

(IV)

For the ergosta-7,22-dien-3β-ol, a molecular formula is $C_{28}H_{46}O$, a relative molecular mass is 398.68, and a chemical structural formula is:

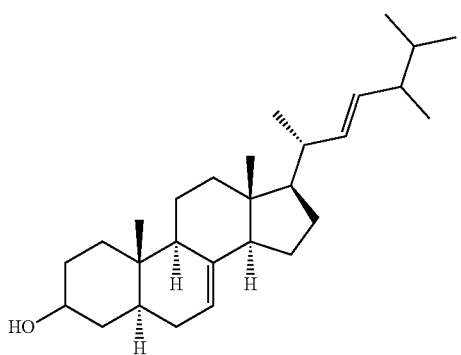

(V)

For the lanosterol, a molecular formula is $C_{30}H_{50}O$, a relative molecular mass is 426.73 and a chemical structural formula is:

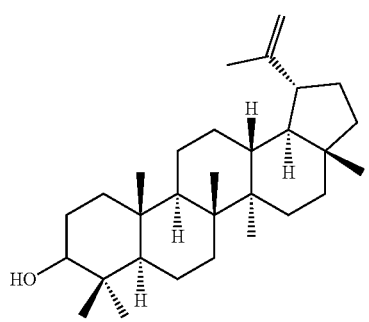

(VI)

For the cholest-7-en-3β,5α-diol, a molecular formula is $C_{27}H_{46}O$, a relative molecular mass is 386.35 and a chemical structural formula is:

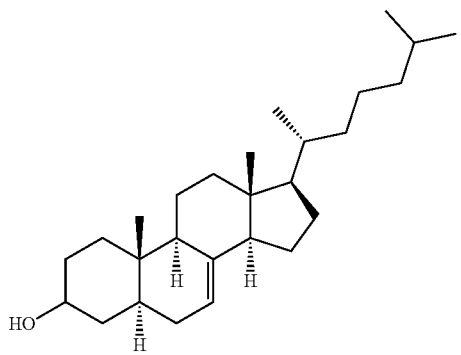

(VII)

The sterol composition in the pumpkin seed oil provided by the preferred embodiment is a pumpkin phytosterol composition extracted from the pumpkin seed oil, wherein: cholesterol, campesterol, β-sitosterol, stigmasterol, ergosta-7,22-dien-3β-ol, lanosterol, and cholest-7-en-3β,5α-diol are all phytosterols; through combining the phytosterol components and controlling a proportion among the components, the effects of alleviating and treating the prostate diseases are achieved, especially for the benign prostatic hyperplasia.

Through cooperation among the phytosterols in the sterol composition in the pumpkin seed oil, the anti-inflammatory effect and the immunomodulatory effect are achieved. Moreover, the phytosterols in the sterol composition in the pumpkin seed oil show high affinity to the prostate tissues and hormonal activity in the animals or human bodies, so that the genetic expressions of the growth factors related to the benign prostatic hyperplasia are regulated without any hormonal side effect. Furthermore, the sterol composition in the pumpkin seed oil is mainly Δ-7 phytosterol, which is the major substance for inhibiting the benign prostatic hyperplasia. The Δ-7 phytosterol has the effect of inhibiting the 5α-reductase, so as to inhibit the testosterone from transforming into the dihydrotestosterone and inhibit the benign prostatic hyperplasia. The sterol composition in the pumpkin seed oil can inhibit not only the expression of 5α-reductase, but also the genetic expressions of androgen receptor, bFGF (basic fibroblast growth factor) and TGF-β1 (transforming growth factor-β1), which is able to obviously decrease the prostate weight and the prostate index, so that the benign prostatic hyperplasia is recovered.

Furthermore, the weight percentages of cholesterol, campesterol, β-sitosterol, stigmasterol, ergosta-7,22-dien-3β-ol, lanosterol, and cholest-7-en-3β,5α-diol are respectively 0.5-1 wt %, 1-3 wt %, 2-3 wt %, 20-35 wt %, 25-35 wt %, 6-8 wt %, and 20-25 wt %.

Furthermore, the weight percentages of cholesterol, campesterol, β-sitosterol, stigmasterol, ergosta-7,22-dien-3β-ol, lanosterol, and cholest-7-en-3β,5α-diol are respectively 0.6-1 wt %, 1.1-2 wt %, 2.2-2.5 wt %, 25-32 wt %, 30-33 wt %, 6-7 wt %, and 22-30 wt %.

In the preferred embodiment, the weight percentages of cholesterol, campesterol, β-sitosterol, stigmasterol, ergosta-7,22-dien-3β-ol, lanosterol, and cholest-7-en-3β,5α-diol are respectively 0.99 wt %, 1.35 wt %, 2.42 wt %, 30.06 wt %, 32.01 wt %, 6.09 wt %, and 24.12 wt %.

In another embodiment, the weight percentages of cholesterol, campesterol, β-sitosterol, stigmasterol, ergosta-7,22-dien-3β-ol, lanosterol, and cholest-7-en-3β,5α-diol are respectively 0.8 wt %, 1.5 wt %, 2.3 wt %, 28 wt %, 31 wt %, 6.5 wt %, and 23 wt %.

In another embodiment, the weight percentages of cholesterol, campesterol, β-sitosterol, stigmasterol, ergosta-7, 22-dien-3β-ol, lanosterol, and cholest-7-en-3β,5α-diol are respectively 2 wt %, 5 wt %, 5 wt %, 40 wt %, 40 wt %, 10 wt %, and 30 wt %.

In another embodiment, the weight percentages of cholesterol, campesterol, β-sitosterol, stigmasterol, ergosta-7, 22-dien-3β-ol, lanosterol, and cholest-7-en-3β,5α-diol are respectively 0.2 wt %, 0.5 wt %, 1.5 wt %, 15 wt %, 20 wt %, 5 wt %, and 30 wt %.

In another embodiment, the weight percentages of cholesterol, campesterol, β-sitosterol, stigmasterol, ergosta-7, 22-dien-3β-ol, lanosterol, and cholest-7-en-3β,5α-diol are respectively 1.5 wt %, 3 wt %, 3.5 wt %, 35 wt %, 30 wt %, 7.5 wt %, and 22.5 wt %.

For above embodiments, the sterol composition in the pumpkin seed oil is a composition extracted from the pumpkin seed oil; the sterol composition in the pumpkin seed oil is prepared through steps of: processing the pumpkin seed oil successively with saponification and organic solvent extraction; taking an extraction upper phase as an extraction liquid; washing the extraction liquid, drying and crystallizing; and obtaining the sterol composition in the pumpkin seed oil.

For the sterol composition in the pumpkin seed oil prepared through the above embodiments, a weight content of the phytosterols therein is above 90%. Compared with the prior art, the purity of the phytosterols prepared through the preferred embodiment of the present invention is higher.

The step of processing the pumpkin seed oil with saponification particularly comprises steps of: preparing 0.5-1.5 mol/L potassium hydroxide-ethyl alcohol solution; combining the pumpkin seed oil and the potassium hydroxide-ethyl alcohol solution with a solid-liquid ratio of 1:10 (w:v); saponifying under reflux at 65-100° C. for 0.5-2.5 hours; after finishing saponifying, obtaining a mixed liquid; adding water into the mixed liquid, wherein a volume fraction of water is 12.5%-25% of that of the mixed liquid; dissolving fatty acid salt generated by saponification; cooling a reaction system to a room temperature, and obtaining a saponification liquid, wherein the room temperature is an environmental temperature of the reaction system.

The step of processing the pumpkin seed oil with organic solvent extraction particularly comprises steps of: adopting n-hexane as an organic solvent; extracting the saponification liquid with n-hexane for 1-3 times; taking the extraction upper phase, merging the extraction upper phase, and obtaining the extraction liquid; wherein: for each time of extraction, a volume ratio of n-hexane to saponification liquid is 1:1.

The step of "washing the extraction liquid" particularly comprises steps of: washing the extraction liquid successively with water, ethanol-water solution, water, potassium hydroxide solution and water; removing a lower aqueous phase and keeping an upper organic phase of the extraction liquid. Furthermore, the step of washing the extraction liquid with potassium hydroxide solution and water is repeated for at least one time, until the lower aqueous phase becomes neutral.

Furthermore, the extraction liquid is washed successively with water, ethanol-water solution with a volume fraction of 8%-25%, water, 0.2-0.5 mol/L potassium hydroxide solution, and water; for each time of washing, washing liquids are respectively water, the ethanol-water solution with the volume fraction of 8%-25%, and 0.2-0.5 mol/L potassium hydroxide solution; a volume of each washing liquid is 10%-30% of a volume of the saponification liquid; the step of washing the extraction liquid with potassium hydroxide solution and water is repeated, until the lower aqueous phase becomes neutral; then the lower aqueous phase is removed, and the upper organic phase of the extraction liquid is kept.

The step of "drying and crystallizing" particularly comprises steps of: merging the upper organic phase; adding anhydrous sodium sulfate into the upper organic phase, and thereafter standing for 10-30 minutes for water removal; concentrating the extraction liquid after water removal through a rotary vacuum evaporator; placing in a refrigerator at 4° C., standing overnight, and obtaining white needle-shaped crystals; processing the white needle-shaped crystals with suction filtration, washing with n-hexane, and drying; and obtaining the sterol composition in the pumpkin seed oil.

During the process of washing after extracting, the saponification liquid obtained through the conventional alkaline saponification method is washed with water and alkali; because the fatty acid salt generated during the saponification process will generate a large amount of foam with water, the upper organic phase in the saponification liquid will be emulsified. Even if the proportion between the lower aqueous phase and the upper organic phase is adjusted, it is unavoidable to form a larger number of emulsion layers between the two phases, which lengthens a washing time to be neutral and causes a loss of the sterol composition in the pumpkin seed oil with washing.

According to the preferred embodiment, during the process of washing the extraction liquid, the ethanol-water solution is added for washing, which effectively prevents the fatty acid salt from generating a large amount of foam with water, and decreases the emulsion layers between the two phases, so that the whole washing process is shortened, the loss of the emulsion layers is decreased, and the final yield is increased. The yield of the above preparation method can reach 1.6-2‰.

In the other hand, the preferred embodiment of the present invention further provides an application of the above sterol composition in the pumpkin seed oil in a drug for treating the benign prostatic hyperplasia.

Through cooperation among the phytosterols in the sterol composition in the pumpkin seed oil, the anti-inflammatory effect and the immunomodulatory effect are achieved. Moreover, the phytosterols in the sterol composition in the pumpkin seed oil show high affinity to the prostate tissues and hormonal activity in the animals or human bodies, so that the genetic expressions of the growth factors related to the benign prostatic hyperplasia are regulated without any hormonal side effect. Furthermore, the sterol composition in the pumpkin seed oil is mainly Δ-7 phytosterol, which is the major substance for inhibiting the benign prostatic hyperplasia. The Δ-7 phytosterol has the effect of inhibiting the 5α-reductase, so as to inhibit the testosterone from transforming into the dihydrotestosterone and inhibit the benign prostatic hyperplasia. The sterol composition in the pumpkin seed oil can inhibit not only the genetic expression of 5α-reductase, but also the genetic expressions of androgen receptor, bFGF and TGF-β1, which is able to obviously decrease the prostate weight and the prostate index, so that the benign prostatic hyperplasia is recovered.

Based on the above application of the sterol composition in the pumpkin seed oil in the drug for treating the benign prostatic hyperplasia, a drug for treating the benign prostatic hyperplasia is further provided, comprising a pharmaceutically acceptable adjuvant and an effective dose of the sterol composition in the pumpkin seed oil.

The effective dose means a therapeutically effective amount, namely an amount of the sterol composition in the pumpkin seed oil beneficial to the individual or having the clinical significance. One skilled in the art will understand that: the actual administration amount or dose, and the administration time depend on the nature and seriousness of the disease to be treated, the age and general conditions of the subject to be treated, the administration way, and so on.

Particularly, the sterol composition in the pumpkin seed oil comprises components by weight percentage of: 0.2-2 wt % cholesterol, 0.5-5 wt % campesterol, 1.5-5 wt % β-sitosterol, 15-40 wt % stigmasterol, 20-40 wt % ergosta-7,22-dien-3β-ol, 5-10 wt % lanosterol, and 15-30 wt % cholest-7-en-3β,5α-diol. In the preferred embodiment, the weight percentages of cholesterol, campesterol, β-sitosterol, stigmasterol, ergosta-7,22-dien-3β-ol, lanosterol, and cholest-7-en-3β,5α-diol are respectively 0.99 wt %, 1.35 wt %, 2.42 wt %, 30.06 wt %, 32.01 wt %, 6.09 wt %, and 24.12 wt %. Through combining the components and controlling a proportion among the components, the effect of the drug for treating the benign prostatic hyperplasia provided by the preferred embodiment on the prostate diseases is improved, especially for the benign prostatic hyperplasia.

The adjuvant should be nontoxic and will not interfere or damage the effect of the sterol composition in the pumpkin seed oil in the above preferred embodiment. Moreover, the adjuvant can be flexibly selected according to the form of the above drug for treating the benign prostatic hyperplasia. Particularly, the adjuvant comprises at least one of saccharide such as lactose, glucose and sucrose, starch such as corn starch and farina starch, malt, gelatin, and talc. According to the form of the drug or the administration way, the adjuvant further comprises lubricant such as lauryl sodium sulfate and magnesium stearate, colorant, releasing agent, coating agent, sweetener, flavoring agent and aromatic. Alternatively, according to the judgment of one skilled in the art, the adjuvant further comprises preservative and antioxidant.

The subject to be treated by the above drug can be animals, including humans. The administration way thereof comprises local, parenteral, intravenous, intra-arterial, intramuscular, and hypodermic injection, aerosol, suppository, and oral administration. The above drug for treating the benign prostatic hyperplasia can be administrated independently or administrated with other composition if necessary.

In the preferred embodiment, according to the administration way of the drug for treating the benign prostatic hyperplasia, the pharmaceutically acceptable adjuvant and the effective dose of the sterol composition in the pumpkin seed oil can be flexibly selected and prepared into different formulations. For example, the above drug for treating the benign prostatic hyperplasia is in any one form of solutions, pills, tablets, capsules, powders, pastes or aerosols.

Correspondingly, according to the preferred embodiment, a method for preparing the above drug for treating the benign prostatic hyperplasia is further provided. The preparation method comprises steps of: processing the pharmaceutically acceptable adjuvant and the effective dose of the sterol composition in the pumpkin seed oil in the drug for treating the benign prostatic hyperplasia according to a method understandable to the pharmacist and a pharmaceutically acceptable technology. Through processing, the drug for treating the benign prostatic hyperplasia in form required by the administration way is prepared. Thus, for the preparation method of the drug for treating the benign prostatic hyperplasia, the adjuvant can be flexibly selected according to formulation requirements; the sterol composition in the pumpkin seed oil, as the effective drug component, can be prepared into the drug with the adjuvant according to the method understandable to the pharmacist and the pharmaceutically acceptable technology, and the preparation technology is stable, which effectively ensures the activity stability of the drug and decreases the production cost.

The present invention is further illustrated with detailed examples as follows.

Example 1

S101: preparing 1.5 mol/L potassium hydroxide-ethyl alcohol solution; combining 180 g pumpkin seed oil with 1800 mL potassium hydroxide-ethyl alcohol solution; saponifying under reflux at 80° C. for 2 hours; after finishing saponifying, obtaining a mixed liquid; adding water into the mixed liquid, wherein a volume fraction of water is 16% of that of the mixed liquid; dissolving fatty acid salt generated by saponification; cooling a reaction system to a room temperature, and obtaining a saponification liquid, wherein the room temperature is an environmental temperature of the reaction system;

S102: extracting the saponification liquid with n-hexane for 2 times; taking an extraction upper phase, merging the extraction upper phase, and obtaining an extraction liquid; wherein: for each time of extraction, a volume ratio of n-hexane to saponification liquid is 1:1;

S103: washing the extraction liquid successively with water, ethanol-water solution with a volume fraction of 20%, water, 0.5 mol/L potassium hydroxide solution, and water; removing a lower aqueous phase, washing until the lower aqueous phase becomes neutral, and keeping an upper organic phase of the extraction liquid; wherein: a volume of each washing liquid is 30% of a volume of the saponification liquid; and S104: merging the upper organic phase; adding anhydrous sodium sulfate into the upper organic phase, and thereafter standing for 10 minutes for water removal; concentrating the extraction liquid after water removal through a rotary vacuum evaporator; placing in a refrigerator at 4° C., standing overnight, and obtaining white needle-shaped crystals; processing the white needle-shaped crystals with suction filtration, washing with n-hexane, and drying; and obtaining the sterol composition in the pumpkin seed oil.

Result Analysis

The sterol composition in the pumpkin seed oil prepared through the example 1 is analyzed and tested by a GC-MS (Gas Chromatography-Mass Spectrometer), and a GC-MS spectrum is obtained. Combined with FIG. 1, components in the example 1 and weight percentages thereof are showed in Table 1, and a phytosterol yield of the sterol composition in the pumpkin seed oil prepared through the example 1 is 1.76‰.

TABLE 1

| Peak | Time (min) | Component | Weight percentage (%) |
| --- | --- | --- | --- |
| 1 | 18.415 | Cholesterol | 0.99 |
| 2 | 19.210 | Campesterol | 1.35 |
| 3 | 19.315 | β-sitosterol | 2.42 |
| 4 | 19.745 | Stigmasterol | 30.06 |
| 5 | 20.500 | Ergosta-7,22-dien-3β-ol | 32.01 |
| 6 | 20.765 | Lanosterol | 6.09 |
| 7 | 21.080 | Cholest-7-en-3β,5α-diol | 24.12 |

Example 2

S201: preparing 1 mol/L potassium hydroxide-ethyl alcohol solution; combining 180 g pumpkin seed oil with 1800 mL potassium hydroxide-ethyl alcohol solution; saponifying under reflux at 70° C. for 2 hours; after finishing saponifying, obtaining a mixed liquid; adding water into the mixed liquid, wherein a volume fraction of water is 16% of that of the mixed liquid; dissolving fatty acid salt generated by saponification; cooling a reaction system to a room temperature, and obtaining a saponification liquid;

S202: extracting the saponification liquid with n-hexane for 2 times; taking an extraction upper phase, merging the extraction upper phase, and obtaining an extraction liquid; wherein: for each time of extraction, a volume ratio of n-hexane to saponification liquid is 1:1;

S203: washing the extraction liquid successively with water, ethanol-water solution with a volume fraction of 20%, water, 0.5 mol/L potassium hydroxide solution, and water; removing a lower aqueous phase, washing until the lower aqueous phase becomes neutral, and keeping an upper organic phase of the extraction liquid; wherein: a volume of each washing liquid is 30% of a volume of the saponification liquid; and S204: merging the upper organic phase; adding anhydrous sodium sulfate into the upper organic phase, and thereafter standing for 10 minutes for water removal; concentrating the extraction liquid after water removal through a rotary vacuum evaporator; placing in a refrigerator at 4° C., standing overnight, and obtaining white needle-shaped crystals; processing the white needle-shaped crystals with suction filtration, washing with n-hexane, and drying; and obtaining the sterol composition in the pumpkin seed oil.

A phytosterol yield of the sterol composition in the pumpkin seed oil prepared through the example 2 is 1.69‰.

Example 3

The animal experiment is made for the sterol composition in the pumpkin seed oil prepared through the example 1.

1. Experimental Grouping

S301: grouping, particularly comprising steps of:

S3011: selecting eighty four-week-old male clean-grade SD (Sprague Dawley) rats having a weight of 200-220 g;

S3012: after feeding the SD rats for one week, selecting ten healthy SD rats as a normal group for blank control, and selecting other fifty healthy SD rats for modeling operation; and S3013: after modeling operation, observing for one week; and dividing the fifty SD rats into five groups, wherein: each group has ten SD rats; the five groups are respectively a model group, a finasteride group, a low-dose group, a medium-dose group, and a high-dose group; the finasteride group adopts the clinical medication such as finasteride tablets for positive control; and the model group is for blank control in the SD rats after modeling operation.

2. Modeling and Administrating

S302: modeling, particularly comprising steps of: S3021: respectively weighing six groups of SD rats;

S3022: except the SD rats of normal group, anesthetizing the SD rats of other five groups (respectively the model group, the finasteride group, the low-dose group, the medium-dose group, and the high-dose group), wherein an anesthetic dose is calculated through equivalent conversion according to body surface areas of humans and animals, and the SD rats are anesthetized through intraperitoneal injection by 10% chloral hydrate according to a dose of 0.3 ml/100 g; after sterilizing the skin of the SD rats, extirpating bilateral testicles, and suturing; intramuscularly injecting penicillin of 200,000 U/(kg·d) at inner thigh muscles of the SD rats for consecutive one week; and observing recovery conditions of the SD rats; and S3023: according to a dose of 4 mg/kg, which is calculated through equivalent conversion according to the body surface areas of humans and animals, hypodermically injecting the testosterone propionate injection to each SD rat for consecutive 30 days, and injecting normal saline of same volume to the SD rats of normal group, so as to finish modeling.

S303: administrating, particularly comprising steps of:

according to an administration dose calculated through equivalent conversion according to the body surface areas of humans and animals, respectively administrating corresponding drugs to the high-dose group, the medium-dose group, the low-dose group, and the finasteride group, and administrating corn oil of same volume to the model group and the normal group, wherein: the high-dose group, the medium-dose group, and the low-dose group all adopt the sterol composition in the pumpkin seed oil prepared through the example 1 for administration. The high-dose group adopts an administration dose of 10 mg/kg (which is calculated through equivalent conversion according to the body surface areas of humans and animals; when the weight of the SD rat is 1 kg, 10 mg of the sterol composition in the pumpkin seed oil prepared through the example 1 is administrated), the medium-dose group adopts an administration dose of 3.3 mg/kg, and the low-dose group adopts an administration dose of 1.1 mg/kg, which respectively correspond to 20 times, 6.66 times, and 2.22 times the clinical dose. Before drug administration, suspensions of 4.5 mg/mL, 1.5 mg/mL, and 0.5 mg/mL are respectively prepared with the corn oil. The finasteride group adopts an administration dose of 0.28 mg/kg. The drug is administrated by gavage once a day; after administrating for consecutive 6 days, administration is stopped for one day; and an administration cycle is 4 week.

3. Index Measurement

Respectively weighing SD rats of six groups two hours after last administration and after fasting for 12 hours;

killing the SD rats, separating the prostate of the SD rats through the tweezers, and weighing the prostate;

fixing a part of the prostate in 10% Formalin solution; embedding the prostate with paraffin, slicing, and staining with HE (hematoxylin-eosin); through an optical microscope, observing morphologic changes of the prostate of the SD rats; and, through an immunohistochemical method, measuring AR (androgen receptor) and SRC-1 (steroid receptor coactivator-1) in the prostate; wherein: the immunohistochemical method is to make positioning, qualitative, and relatively quantitative researches for the indexes according to a specific binding reaction between the measured index such as protein and the antibody, so as to show the expression quantity and the expression location of the protein;

rapidly placing the other part of the prostate in liquid nitrogen; and, through a RT-qPCR (Reverse transcription-qPCR) technology, measuring expressions of 5α-reductase, AR, bFGF (basic fibroblast growth factor) mRNA (Messenger RNA), TGF-β1 (transforming growth factor-β1) mRNA, and Bcl-2 (B-cell lymphoma-2).

4. Result Analysis

The results of the influences of the sterol composition in the pumpkin seed oil prepared through the example 1 on the benign prostatic hyperplasia rats treated with testosterone propionate are showed in Table 2.

TABLE 2

Influences of sterol composition in pumpkin seed oil prepared through example 1 on prostate index

| Group | Rat weight (g) | Prostate weight (mg) | Prostate index (mg/100 g) |
|---|---|---|---|
| Normal group | 450.4 ± 47.7 | 835.6 ± 161.9 | 185.6 ± 29.5 |
| Model group | 415.8 ± 25.1 | 1072.9 ± 61.9** | 258.8 ± 21.0** |
| Finasteride group | 439.2 ± 32.7 | 868.4 ± 188.3# | 198.1 ± 44.3## |
| Low-dose group | 427.1 ± 34.0 | 1002.4 ± 141.9* | 235.3 ± 34.1** |
| Medium-dose group | 421.2 ± 48.9 | 875.1 ± 132.2## | 210.6 ± 41.1## |
| High-dose group | 426.5 ± 26.8 | 852.7 ± 144.6## | 199.7 ± 29.0## |

In the table: prostate index = prostate weight (mg)/rat weight (100 g);
*represents there exists an obvious difference compared with the normal group, $P < 0.05$; and,
**represents there exists a greatly obvious difference compared with the normal group, $P < 0.01$; and
represents there exists an obvious difference compared with the model group, $P < 0.05$; and,
represents there exists a greatly obvious difference compared with the model group, $P < 0.01$.

It can be seen from Table 2 that: the weight of each group of rats has no obvious change; compared with the normal group, the prostate weight and the prostate index of the model group are obviously increased, respectively by 28.4% and 39.4%; compared with the model group, the prostate weight and the prostate index of the finasteride group are decreased respectively by 19.1% and 23.5%; compared with the model group, the prostate indexes of the medium-dose group and the high-dose group are obviously decreased, respectively by 18.4% and 20.5%; the high-dose group and the medium-dose group basically reach the effect of the finasteride group.

Figure 2:
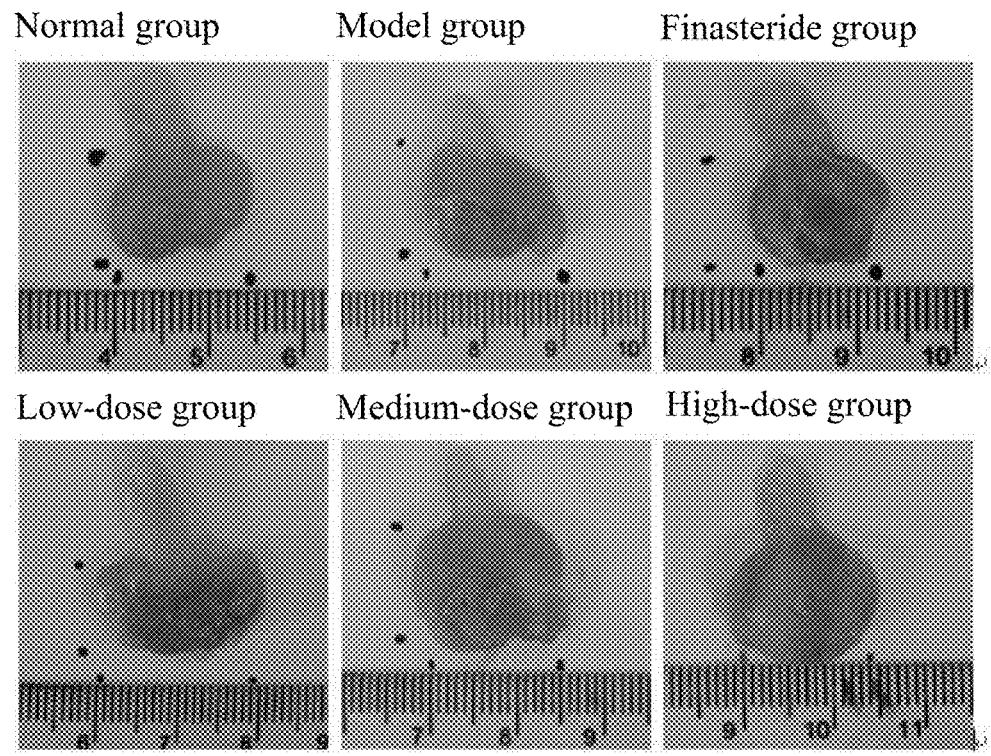
FIG. 2 shows prostate tissues of six groups according to example 3 of the present invention.

FIG. 2 shows prostate tissues of six groups. For the normal group, the surface of the prostate tissue is smooth, and the color is pink. For the model group, the volume of the prostate tissue is larger than that of the normal group; the color is darker and is dark red; and, the surface of the prostate tissue has hyperplasia nodule bumps. Compared with the model group, the volumes of the prostate tissues of the finasteride group, the high-dose group and the medium-dose group are obviously decreased. For the high-dose group, the surface of the prostate tissue becomes smooth and has no obvious hyperplasia nodules, which basically recovers to the condition of the normal group.

Figure 3:
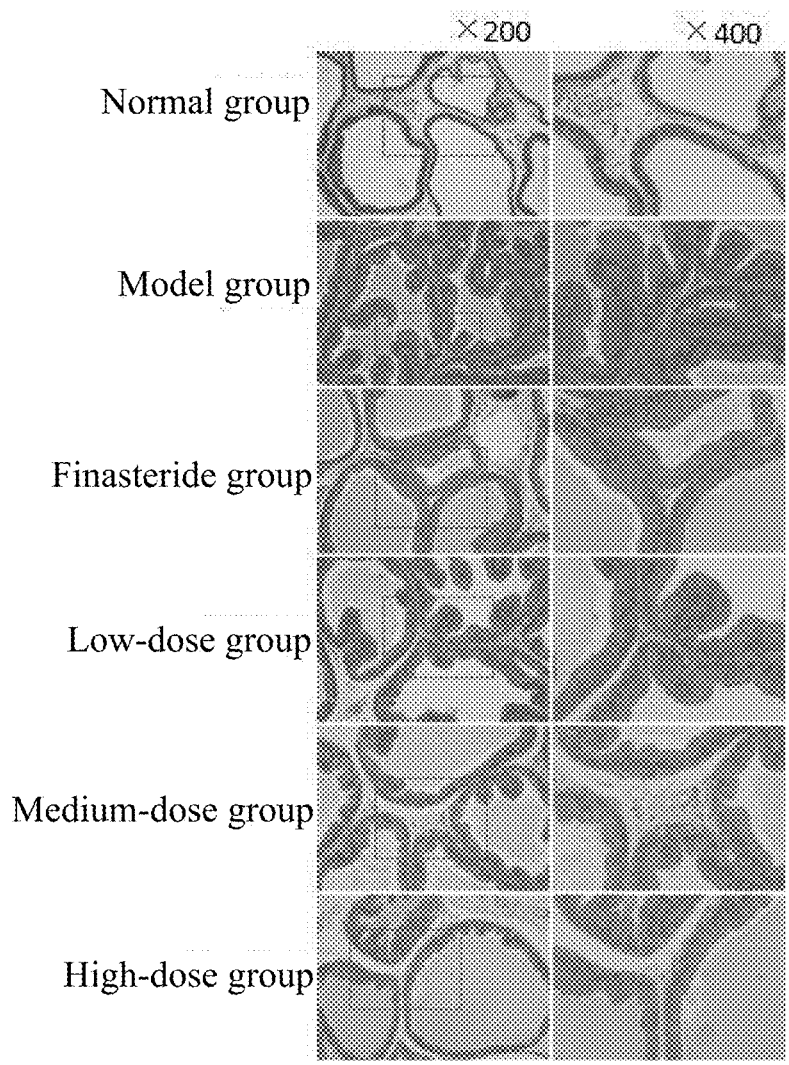
FIG. 3 shows HE (hematoxylin-eosin) stain pathological slices of six groups according to the example 3 of the present invention.

FIG. 3 shows HE stain pathological slices of six groups; in FIG. 3, the magnification in the left side is 200 times, and the magnification in the right side is 400 times; and the prostate tissues are evaluated through HE stain. For the model group, compared with the normal group, the epithelial cells of the prostate are obviously proliferated from single layer to multiple layers, the cavity area is obviously decreased, and the cavity space becomes tight. Through treating with finasteride and the sterol composition in the pumpkin seed oil prepared through the example 1, for the finasteride group, the low-dose group, the medium-dose group and the high-dose group, part of the multiple-layer epithelial cells in the prostate tissue recover to the single-layer epithelial cells, the cavity area is increased, and the cavity space becomes loose.

Figure 4:
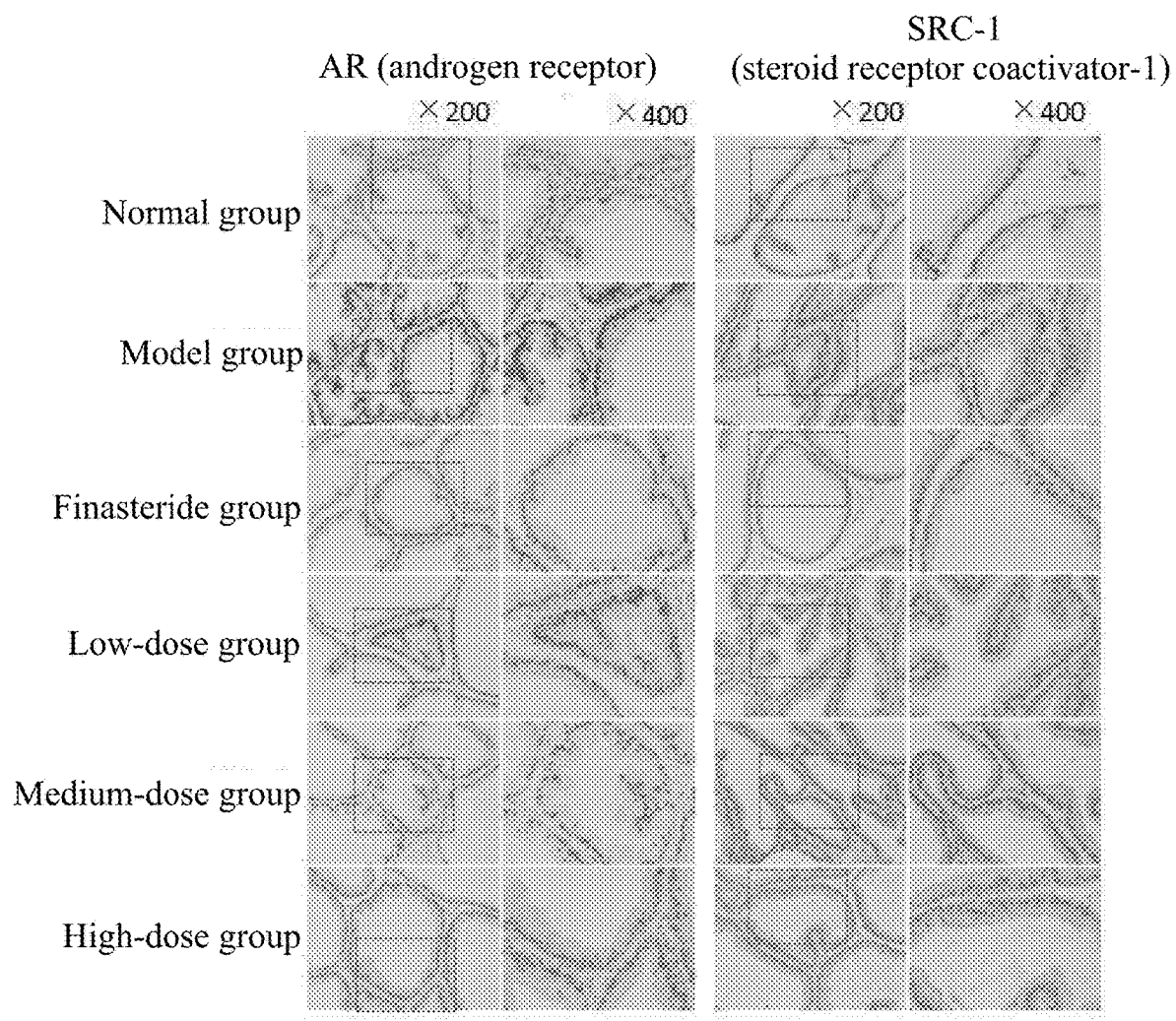
FIG. 4 shows influences of the sterol composition in the pumpkin seed oil prepared through the example 1 on expressions of AR (androgen receptor) and SRC-1 (steroid receptor coactivator-1) of benign prostatic hyperplasia rats according to the example 3 of the present invention.

FIG. 4 shows influences of the sterol composition in the pumpkin seed oil prepared through the example 1 on expressions of AR and SRC-1 of the benign prostatic hyperplasia rats, wherein: in FIG. 4, the magnification in the left side is 200 times, and the magnification in the right side is 400 times.

Through the immunohistochemical method, the genetic expressions of the factors related to the benign prostatic hyperplasia, such as AR and SRC-1, are evaluated. Under the effect of 5α-reductase, the testosterone is transformed into the dihydrotestosterone; the testosterone can bind with AR and SRC-1, and the dihydrotestosterone can also bind with AR and SRC-1; the binding ability of the dihydrotestosterone with AR is five times the binding ability of the testosterone with AR; and the dihydrotestosterone is the major cause of stimulating the benign prostatic hyperplasia. Thus, through inhibiting the genetic expression of 5α-reductase, the benign prostatic hyperplasia can be effectively controlled. Finasteride can effectively inhibit the genetic expression of 5α-reductase.

The genetic expression quantities of AR and SRC-1 in the model group is obviously higher than that of the normal group; and, for the finasteride group and the high-dose group, medium-dose group and low-dose group treated with the sterol composition in the pumpkin seed oil prepared through the example 1, the genetic expressions of AR and SRC-1 are all obviously decreased.

Figure 5:
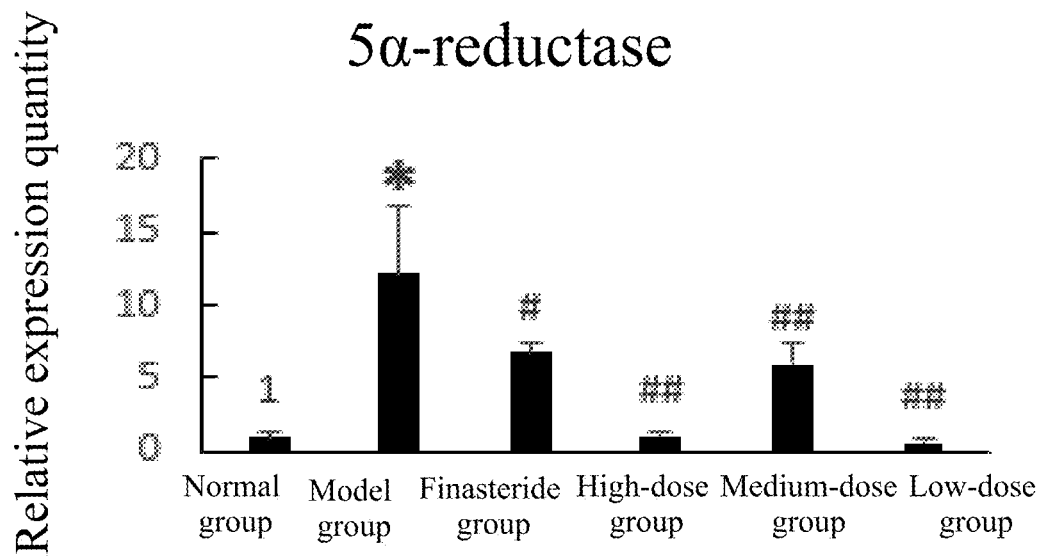
FIG. 5 is a genetic expression change diagram of 5α-reductase tested with RT-qPCR (Reverse transcription-qPCR) according to the example 3 of the present invention.
Figure 6:
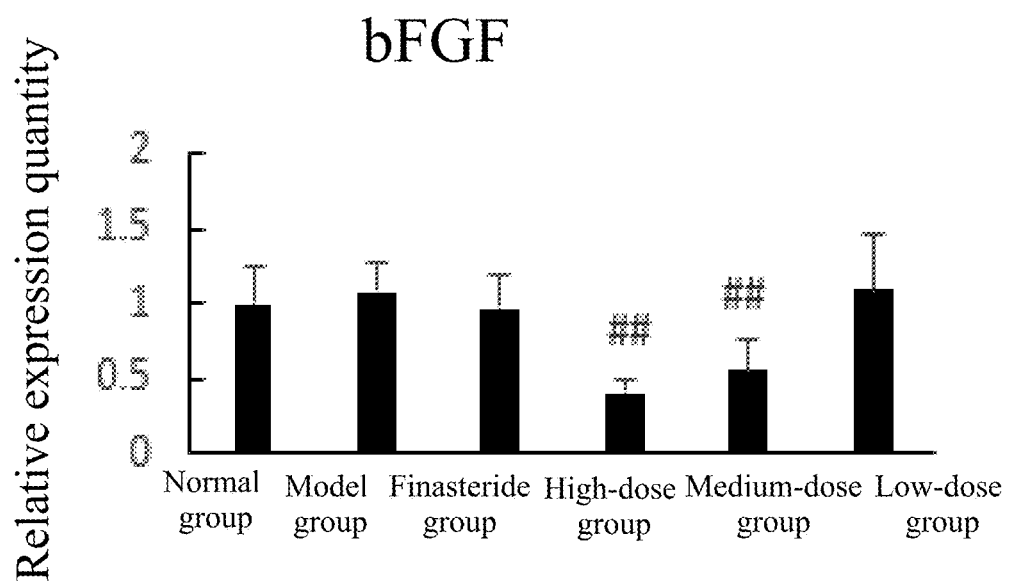
FIG. 6 is a genetic expression change diagram of bFGF (basic fibroblast growth factor) tested with RT-qPCR according to the example 3 of the present invention.
Figure 7:
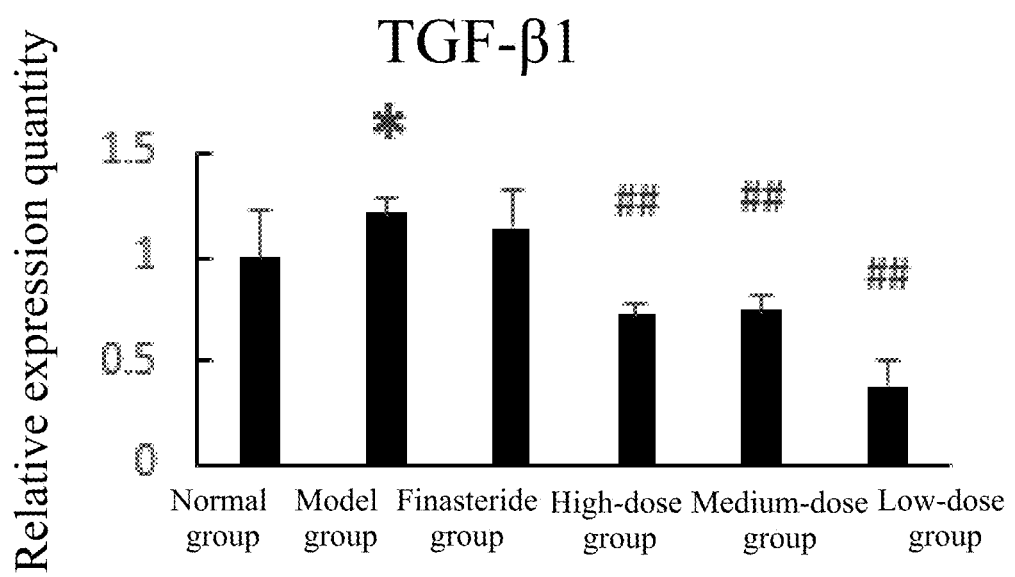
FIG. 7 is a genetic expression change diagram of TGF-β1 (transforming growth factor-β1) tested with RT-qPCR according to the example 3 of the present invention.

Combined with FIG. 5-FIG. 7, genetic expression change diagrams of the growth factors related to the benign prostatic hyperplasia and 5α-reductase tested with RT-qPCR are showed.

The growth factor is a kind of small molecule peptide, and various kinds of growth factors exist in the prostate, such as bFGF and TGF-β1. The genetic expressions of the growth factor all have regulation effects on growth, differentiation, proliferation and apoptosis of the prostatic cells.

5α-reductase is the key enzyme for transforming the testosterone into the dihydrotestosterone. The genetic expression quantity of 5α-reductase of the model group is obviously higher than that of the normal group. Compared with the model group, the genetic expression quantity of 5α-reductase of the finasteride group is obviously decreased. The genetic expression quantities of 5α-reductase of the high-dose group, medium-dose group and low-dose group treated with the sterol composition in the pumpkin seed oil prepared through the example 1 are obviously decreased.

bFGF is the important factor for promoting the mitosis in the mesoblast and nerve ectoderm cells. In the prostate tissue, bFGF is mainly for stimulating the proliferation of the matrix cells, and the over-expression of bFGF may be one pathogenesis of the benign prostatic hyperplasia. The relative genetic expression quantity of bFGF of the model group is higher than that of the normal group; and, the high-dose group and the medium-dose group obviously decrease the genetic expression of bFGF in the prostate tissue. With the increase of drug concentration, the control effect on the genetic expression of bFGF becomes better.

TGF-β1 is a kind of polypeptide having the wide biological activity, which has regulation effects on proliferation, development, transformation and differentiation of the cells in the prostate tissue. TGF-β1 has double effects of stimulating and inhibiting the mitosis. TGF-β1 can inhibit the growth of mesenchymal cells, induce the expression of smooth muscle cell phenotype, and promote the differentiation of the mesenchymal cells to the smooth muscle cells. The enhancement of the negative control effect of TGF-β1 in the matrix and epithelial cells of the prostate combined with the reduction of the positive control effect of bFGF can accelerate the apoptosis in the prostate tissue and the atrophy of the prostate tissue.

Through cooperation among the phytosterols in the sterol composition in the pumpkin seed oil, the anti-inflammatory effect and the immunomodulatory effect are achieved. Moreover, the phytosterols in the sterol composition in the pumpkin seed oil show high affinity to the prostate tissues and hormonal activity in the SD rats, so that the genetic expressions of the growth factors related to the benign prostatic hyperplasia are regulated without any hormonal side effect. Furthermore, the sterol composition in the pumpkin seed oil is mainly Δ-7 phytosterol, which is the major substance for inhibiting the benign prostatic hyperplasia. The Δ-7 phytosterol has the effect of inhibiting the 5α-reductase, so as to inhibit the testosterone from transforming into the dihydrotestosterone and inhibit the benign prostatic hyperplasia. The sterol composition in the pumpkin seed oil can inhibit not only the expression of 5α-reductase, but also the genetic expressions of androgen receptor, bFGF and TGF-β1, which is able to obviously decrease the prostate weight and the prostate index, so that the benign prostatic hyperplasia is recovered.

The above-mentioned is only the preferred embodiment of the present invention, not for limiting the present invention. Modifications, equivalent replacements and improvements made within the spirit and principle of the present invention are all included in the protection scope of the present invention.

What is claimed is:

1. A method for preparing a sterol composition from pumpkin seed oil comprising:
   a) preparing 0.5-1.5 mol/L of a potassium hydroxide-ethanol solution; combining the pumpkin seed oil and the potassium hydroxide-ethyl alcohol solution with a solid-liquid ratio of 1:10 (w:v); saponifying under reflux at 65° C.-100° C. for 0.5-2.5 hours; after finishing saponifying, obtaining a mixed liquid; adding water into the mixed liquid, wherein a volume fraction of water is 12.5%-25% of that of the mixed liquid; dissolving the fatty acid salt generated by saponification; cooling the reaction system to a room temperature, and obtaining a saponification liquid,
   b) washing the saponification liquid successively with water, an ethanol-water solution, water, potassium hydroxide solution and water; removing the lower aqueous phase of the saponification liquid and keeping the upper organic phase of the saponification liquid;
   c) taking the upper phase of the saponification liquid;
   d) washing the upper phase, drying and then crystallizing the upper phase to obtain the sterol composition from the pumpkin seed oil, wherein the sterol composition from the pumpkin seed oil comprises 0.2 wt. %-2 wt. % cholesterol, 0.5 wt. %-5 wt. % campesterol, 1.5 wt. %-5 wt. % B-sitosterol, 15 wt. %-40 wt. % stigmasterol, 20 wt. %-40 wt. % ergosta-7,22-dien-3 beta-ol, 5 wt. %-10 wt. % lanosterol and 15 wt. %-30 wt. % cholest-7-en-3 beta,5 alpha-diol.

* * * * *